(12) United States Patent
Haushalter et al.

(10) Patent No.: US 9,651,496 B2
(45) Date of Patent: *May 16, 2017

(54) RARE EARTH DOWNCONVERTING PHOSPHOR COMPOSITIONS FOR OPTICALLY ENCODING OBJECTS AND METHODS AND APPARATUS RELATING TO SAME

(71) Applicant: Parallel Synthesis Technologies, Santa Clara, CA (US)

(72) Inventors: Robert W. Haushalter, Los Gatos, CA (US); Robert C. Haushalter, Los Gatos, CA (US)

(73) Assignee: Parallel Synthesis Technologies, Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/530,074

(22) Filed: Oct. 31, 2014

(65) Prior Publication Data

US 2015/0192522 A1    Jul. 9, 2015

Related U.S. Application Data

(62) Division of application No. 11/577,697, filed as application No. PCT/US2005/038638 on Oct. 24, 2005, now Pat. No. 8,927,892.

(Continued)

(51) Int. Cl.
*G01N 21/64* (2006.01)
*G01N 33/68* (2006.01)

(52) U.S. Cl.
CPC ........ *G01N 21/6486* (2013.01); *G01N 21/643* (2013.01); *G01N 21/6456* (2013.01); *G01N 33/68* (2013.01); *G01N 2021/6441* (2013.01)

(58) Field of Classification Search
CPC ......... G01N 2021/6441; G01N 21/643; G01N 21/6456; G01N 21/6486; G01N 33/20; G01N 33/68

(Continued)

(56) References Cited

U.S. PATENT DOCUMENTS 3,250,722 A    5/1966   Borchardt
3,412,245 A    11/1968  Halverson
(Continued)

FOREIGN PATENT DOCUMENTS

EP    1491350 A2    12/2004
EP    1491350 A3    8/2005
(Continued)

OTHER PUBLICATIONS

Related U.S. Appl. No. 12/091,900, "Final Office Action", Apr. 22, 2011, Publisher: USPTO, Published in: US.

(Continued)

*Primary Examiner* — Maureen Wallenhorst
(74) *Attorney, Agent, or Firm* — Kaplan Breyer Schwarz & Ottesen, LLP

(57) ABSTRACT

A rare earth (RE) downconverting phosphor composition may contain two or more lanthanide materials each having a host and at least one downconverting emitter. Each lanthanide material emits a detectable electromagnetic radiation emission peak at an intensity, which is proportional to the amount of emitter present, upon excitation with an absorbable electromagnetic radiation, the emitted radiation having a lower energy, i.e., a longer wavelength than the absorbable radiation. One or more ratios of the intensities of the emitted detectable electromagnetic radiation may be used to uniquely identify the composition. Alternatively, the RE downconverting phosphor composition may contain a lanthanide material having a host and at least two emitters.

(Continued)

The lanthanide material emits at least two different detectable electromagnetic radiation emission peaks each at an intensity upon excitation with an absorbable electromagnetic radiation, the emitted radiation having a lower energy, i.e., a longer wavelength than the absorbable radiation.

30 Claims, 6 Drawing Sheets

Related U.S. Application Data

(60) Provisional application No. 60/621,402, filed on Oct. 22, 2004.

(58) Field of Classification Search
USPC ... 436/501, 518, 524, 525, 527, 531, 73, 81, 436/82, 86, 94, 164, 166, 172; 422/52, 422/82.05, 82.08; 435/6.1, 7.1, 7.2; 209/587; 252/301.4 R, 301.4 H, 301.4 S, 252/301.6 S, 301.36; 506/9; 977/774
See application file for complete search history.

(56) References Cited

U.S. PATENT DOCUMENTS

| | | | |
|---|---|---|---|
| 3,473,027 A | 10/1969 | Philips et al. | |
| 4,018,635 A | 4/1977 | Ryan et al. | |
| 4,491,620 A | 1/1985 | Joiner, Jr. | |
| 4,816,344 A | 3/1989 | Chiang | |
| 5,043,265 A | 8/1991 | Tanke et al. | |
| 5,329,127 A | 7/1994 | Becker et al. | |
| 5,674,698 A * | 10/1997 | Zarling | G01N 33/588 422/504 |
| 5,698,397 A | 12/1997 | Zarling et al. | |
| 5,891,656 A | 4/1999 | Zarling et al. | |
| 6,159,686 A | 12/2000 | Kardos et al. | |
| 6,201,989 B1 | 3/2001 | Whitehead et al. | |
| 6,207,130 B1 | 3/2001 | Kareiva et al. | |
| 6,399,397 B1 | 6/2002 | Zarling et al. | |
| 6,403,947 B1 | 6/2002 | Hoyt et al. | |
| 6,500,622 B2 * | 12/2002 | Bruchez, Jr. | B82Y 5/00 435/6.11 |
| 6,514,295 B1 | 2/2003 | Chandler et al. | |
| 6,536,672 B1 | 3/2003 | Outwater | |
| 6,537,829 B1 | 3/2003 | Zarling et al. | |
| 6,552,290 B1 | 4/2003 | Lawandy | |
| 6,692,031 B2 | 2/2004 | McCrew | |
| 7,309,568 B2 | 12/2007 | Oshida et al. | |
| 8,673,107 B2 | 3/2014 | Haushalter | |
| 8,796,030 B2 | 8/2014 | Haushalter | |
| 8,927,892 B2 * | 1/2015 | Haushalter | G01N 21/643 209/587 |
| 2001/0049101 A1 | 12/2001 | Brogger et al. | |
| 2002/0022273 A1 | 2/2002 | Empedocles et al. | |
| 2002/0025490 A1 | 2/2002 | Shchegolikhin et al. | |
| 2002/0041372 A1 | 4/2002 | Gardner et al. | |
| 2003/0002029 A1 | 1/2003 | Dukler et al. | |
| 2003/0098357 A1 | 5/2003 | Cummings et al. | |
| 2003/0129296 A1 | 7/2003 | Kelso | |
| 2003/0180482 A1 | 9/2003 | Narita et al. | |
| 2003/0207331 A1 * | 11/2003 | Wilson, Jr. | B01J 19/0046 435/7.1 |
| 2004/0072233 A1 | 4/2004 | Kauvar et al. | |
| 2004/0099740 A1 | 5/2004 | Chresand et al. | |
| 2004/0217298 A1 | 11/2004 | Bawendi et al. | |
| 2004/0217364 A1 | 11/2004 | Tarsa et al. | |
| 2005/0056183 A1 | 3/2005 | Meshirer | |
| 2005/0136486 A1 * | 6/2005 | Haushalter | B82Y 5/00 435/7.2 |
| 2005/0208543 A1 * | 9/2005 | Vann | B82Y 5/00 435/6.12 |
| 2007/0011023 A1 | 1/2007 | Silverbrook | |
| 2007/0059705 A1 * | 3/2007 | Lu | B82Y 15/00 435/6.11 |
| 2009/0117340 A1 | 5/2009 | Halfyard et al. | |
| 2009/0218805 A1 | 9/2009 | Haushalter | |

FOREIGN PATENT DOCUMENTS

| | | |
|---|---|---|
| WO | 2006047621 A1 | 5/2006 |
| WO | 2007051035 A1 | 5/2007 |

OTHER PUBLICATIONS

Sonya Mazumdar, "Related U.S. Appl. No. 12/091,900", "Non-Final Office Action", Apr. 26, 2010, Publisher: USPTO, Published in: US.
"Related U.S. Appl. No. 10/890,530", "Non-Final Office Action", Oct. 29, 2009, Publisher: USPTO, Published in: US.
"Related U.S. Appl. No. 10/890,530", "Final Office Action", Dec. 13, 2011, Publisher: USPTO, Published in: US.
"International Patent Application No. PCTUS05/24174, International Search Report & Written Opinion", Feb. 14, 2007, Publisher: USPTO, Published in: US.
"International Patent Application No. PCT/US05/38638 International Search Report & Written Opinion", Apr. 4, 2006, Publisher: USPTO, Published in: US.
"Related U.S. Appl. No. 10/890,530", "Final Office Action", Mar. 13, 2009, Publisher: USPTO, Published in: US.
"Related U.S. Appl. No. 10/890,530", "Non-Final Office Action", Mar. 30, 2011, Publisher: USPTO, Published in: US.
"Related U.S. Appl. No. 10/890,530", "Final Office Action", Jul. 21, 2010, Publisher: USPTO, Published in: US.
"Co-Pending U.S. Appl. No. 10/890,530", "Non-Final Office Action", Apr. 24, 2014, Publisher: USPTO, Published in: US.
"Co-Pending U.S. Appl. No. 10/890,530", "Non-Final Office Action", Jun. 21, 2013, Publisher: USPTO, Published in: US.
"Related U.S. Appl. No. 10/890,530", "Non-Final Office Action", Jul. 28, 2008, Publisher: USPTO, Published in: US.
"Related U.S. Appl. No. 11/577,697", "Non-Final Office Action", Apr. 26, 2012, Publisher: USPTO, Published in: US.
"Related U.S. Appl. No. 11/577,697", "Final Rejection", Jun. 27, 2014, Publisher: USPTO, Published in: US.
"Related U.S. Appl. No. 11/577,679", "Non-Final Office Action", Aug. 30, 2013, Publisher: USPTO, Published in: US.
"Related U.S. Appl. No. 11/577,697", "Restriction Requirement", Oct. 6, 2011, Publisher: USPTO, Published in: US.
"Related EP Application No. 05813069.1-2204", "EP Office Action", Oct. 5, 2011, Publisher: EPO, Published in: EP.
"Related U.S. Appl. No. 12/091,900", "Final Office Action", Sep. 17, 2012, Publisher: USPTO, Published in: US.
"Related U.S. Appl. No. 12/091,900", "Non-Final Office Action", Dec. 15, 2011, Publisher: USPTO, Published in: US.
Davide D'Alessandro, "Related EP Application No. 05813069.1", "Extended European Search Report", Aug. 5, 2009, Publisher: EPO, Published in: EP.
W. H. Wright, et al., "Flow Cytometry with Upconverting Phosphors Reporters", "Optical Investigations of Cells in Vitro and In Vivo, D.L. Farkas, et al", Apr. 1998, pp. 245-254, vol. 3260, Publisher: SPIE, Published in: US.
"International Search Report and Written Opinion ", Feb. 21, 2007, Publisher: ISA/US, Published in: US.
Simon Officer et al., "Novel online security system based on rare-earth doped glass micro beads", "The International Society for Optical Engineering", Jan. 20, 2004, pp. 387-395, vol. 5310, No. 1, Publisher: Proceedings of the SPIE, Published in: US.
Matthew J. Dejneka, et al, "Rare earth-doped glass microbarcodes", "National Academy of Science, Washington DC", Jan. 21, 2003, pp. 389-393, vol. 100, No. 2, Publisher National Academy of Sciences of USA, Published in: US.
"Notice of Allowance", dated Jun. 20, 2014, issued in parent U.S. Appl. No. 10/890,530.

(56) References Cited

OTHER PUBLICATIONS

"Decision to refuse a European Patent Application", dated Oct. 25, 2003, issued in Related EP Application No. 05813069.1 (counterpart to U.S. Appl. No. 11/577,697).
"Summons to attend oral proceedings pursuant to Rule 115(1) EPC", dated May 3, 2013, issued in related EP Application No. 05813069.1 (counterpart to U.S. Appl. No. 11/577,697).
"Notice of Allowance", dated Sep. 2, 2014, issued in related U.S. Appl. No. 11/577,697.
"Supplemental Notice of Allowance", dated Sep. 18, 2014, issued in related U.S. Appl. No. 11/577,697.
"Notice of Allowance", dated Oct. 25, 2013, issued in related U.S. Appl. No. 12/091,900.
"Definition of 'print'"—Merriam-Webster Dictionary; Dec. 2011.
"Non-Final Office Action", dated Apr. 9, 2015, issued in related U.S. Appl. No. 14/446,139.
"Final Office Action", dated Nov. 30, 2015, issued in related U.S. Appl. No. 14/446,139.
"Advisory Action", dated Mar. 3, 2016, issued in related U.S. Appl. No. 14/446,139.
"Notice of Allowance", dated May 16, 2016, issued in related U.S. Appl. No. 14/446,139.

\* cited by examiner

US 9,651,496 B2

RARE EARTH DOWNCONVERTING PHOSPHOR COMPOSITIONS FOR OPTICALLY ENCODING OBJECTS AND METHODS AND APPARATUS RELATING TO SAME

RELATED APPLICATIONS

This application is a divisional of U.S. application Ser. No. 11/577,697, filed Mar. 4, 2009, now U.S. Pat. No. 8,927,892, which is a National Stage of International Application No. PCT/US2005/038638, filed Oct. 24, 2005, which claims the benefit of U.S. Provisional Application No. 60/621,402, filed Oct. 22, 2004. The entire disclosures of U.S. application Ser. No. 11/577,697, International Application No. PCT/US2005/038638, and U.S. Provisional Application No. 60/621,402 are incorporated herein by reference.

FIELD OF THE INVENTION

The present invention relates to optical encoding. More specifically, the present invention relates to rare earth downconverting phosphor compositions for optically encoding objects and methods and apparatus relating to same. The compositions are capable of generating a unique optical spectrum or unique optical signature from which an optical code or barcode can be calculated.

BACKGROUND OF THE INVENTION

The authentication of objects including without limitation, documents, money, people and valuables, has been an important endeavor for thousands of years. It will, similarly to encryption and code breaking, continue to be a significant and constantly evolving problem for the indefinite future. While a great deal of effort has been expended with respect to the development of Information Technology related security issues, the physical encoding of samples to identify, track and validate objects or samples is also critically important. The considerable financial and physical losses that result from counterfeiting and the lack of widespread, accurate and inexpensive authentication technology permeate every aspect of society. Examples include document forgeries, illegal duplication of software and optical media, branded consumer goods, technical intellectual property theft and pharmaceutical tampering.

There are also other classes of objects or samples that are in need of rapid and precise identification, for example, large numbers of biological samples. There are many advantages to using an encoded particle system instead of existing chip-based formats to investigate large number of samples.

One method to identify objects is to optically encode them, i.e., combine an object with an optically active material which is capable of emitting an identifiable, unique spectral or optical signal or signature when suitably excited. Previously known systems for optically encoding objects or samples have a fundamental problem: they cannot support a very large number of unique codes, which means only small numbers of samples can be measured or identified. A unique identifying code is related to a unique optical emission signature. In many cases, the optical code is generated by observing ratios of two or more emitting components in a mixture. However, if the emitters are organic dyes or quantum dots instead of lanthanide emitters, their short, excited state lifetimes lead to broad emission peaks, each of which can occupy a large swath of the visible spectrum. Therefore, when two or more components are mixed to create a desired ratio that emits a code of interest, it is difficult to deconvolute the broad overlapping peaks. This is starkly reflected in the most extensive, commercially available codes, which currently consist of (a) only two dyes resolvable at 1% compositional intervals giving a maximum of 100 samples that can be labeled uniquely and (b) mixtures of quantum dots (QD) where up to only 180 individuals codes are reported to be available.

Therefore, there exists a significant need in the art for compositions and methods for optically encoding an object or sample such that truly large numbers of codes can be obtained and used to encode very large numbers of objects or samples which can then be uniquely identified.

BRIEF DESCRIPTION OF THE DRAWINGS

FIG. 1A depicts the downconverter emitters. FIG. 1B is a graph illustrating a spectrum generated by the composition combined with the object, after excitation with energy of a predetermined wavelength. FIG. 1C is a graph showing measurements of the relative integrated intensity of the various colors of light emitted by the composition combined with the object. FIG. 1D is a graph showing the optical barcode generated from ratios of the intensities of the various colors of light emitted by the composition combined with the object.

DETAILED DESCRIPTION OF THE INVENTION

Figure 1:
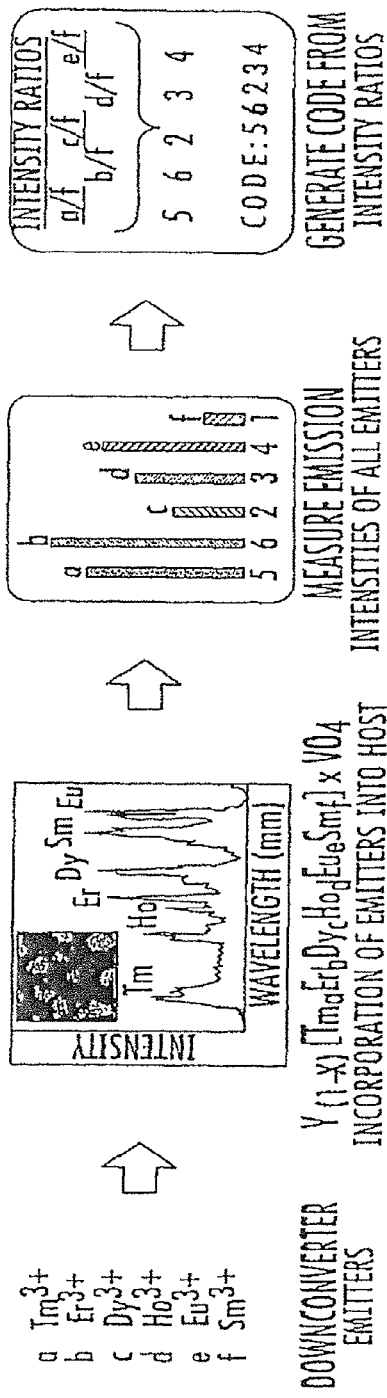
FIGS. 1A-1D illustrate an exemplary method for generating an optical signature or "barcode" from light emitted by a rare earth downconverting phosphor composition of the invention, which has been combined with an object.

As used herein, the following terms are defined:

"Reporter" refers to a chemical substituent attached to or associated with a probe that produces, under appropriate excitation conditions, a detectable optical signal, wherein the signal indicates the presence of the probe.

"Target" refers to an object that can be assayed using various methods. Examples of targets include, without limitation, polypeptides, glycoproteins, viruses, carbohydrates, cells, microorganisms, polynucleotides and pharmaceuticals.

"Probe" refers to a binding component that binds preferentially to one or more targets (e.g., antigenic epitopes, polynucleotide sequences, macromolecular receptors) with an affinity sufficient to permit discrimination of reporter-probe combination to target from a nonspecifically bound reporter-probe combination (i.e., background).

"Lanthanide Materials" refers to materials containing elements 57-70.

"Rare earth (RE) downconverting phosphor composition" refers to a luminescent material containing one or more rare earths or lanthanides. In all cases "downconverting" refers to a composition or material that emits light of a longer wavelength, or lower energy, than that of the excitation radiation.

"Thermolysis" refers to the thermal decomposition of molecular or polymeric precursors into a solid state material (e.g., yttrium nitrate undergoing thermolysis to yttrium oxide plus nitrogen oxides). In some embodiments, the precursors for the RE downconverting phosphor compositions are soluble in water or other solvents.

It is important to note the distinction between an optical emission from a reporter or reporter-probe-target complex, which generally provides an indication that a certain chemical reaction has occurred, and the light emitted from encoded material or objects containing downconverting phosphor compositions. Light emitted from the downconverting compositions provides a means of identifying or distinguishing the encoded object.

The present invention comprises an optical encoding method that substantially exceeds current technology in terms of accuracy, depth of multiplexing (i.e. number of resolvable optical signatures or barcodes) and speed of analysis. One aspect of the present invention comprises rare earth (RE) downconverting phosphor compositions, each of which is capable of generating a unique optical spectrum or unique optical signature from which an optical code or barcode can be derived. In one exemplary embodiment, the RE downconverting phosphor composition may comprise two or more lanthanide materials. Each lanthanide material may comprise a host and at least one downconverting emitter. In some embodiments, the host may capable of absorbing the excitation radiation directly itself. In other embodiments, the host may contain a constituent that absorbs excitation radiation, and must contain such a constituent if it is not capable of absorbing excitation radiation directly. Each of the lanthanide materials emits a detectable electromagnetic radiation emission peak at an intensity, which is proportional to the amount of emitter present, upon excitation with an absorbable electromagnetic radiation, the emitted radiation comprising a lower energy, i.e., a longer wavelength than the absorbable radiation. In one exemplary embodiment, the emitted radiation comprises a wavelength of less than 850 nanometers and the absorbable radiation comprises a wavelength of less than 450 nanometers. One or more relative ratios of the intensities of the emitted detectable electromagnetic radiation may be used to uniquely identify the composition.

In another exemplary embodiment, the RE downconverting phosphor composition may comprise a lanthanide material comprising a host and at least two emitters. The host, in some embodiments, may be capable of absorbing excitation radiation directly itself. In other embodiments, the host may contain a constituent that absorbs excitation radiation, and must contain such a constituent if it is not capable of absorbing excitation radiation directly. The lanthanide material emits at least two different detectable electromagnetic radiation emission peaks each at an intensity upon excitation with an absorbable electromagnetic radiation, the emitted radiation comprising a lower energy, i.e., a longer wavelength than the absorbable radiation. In one exemplary embodiment, the emitted radiation comprises a wavelength of less than 850 nanometers and the absorbable radiation comprises a wavelength of less than 450 nanometers. One or more relative ratios of the intensities of the emitted detectable electromagnetic radiation may be used to uniquely identify the composition.

Figure 2:
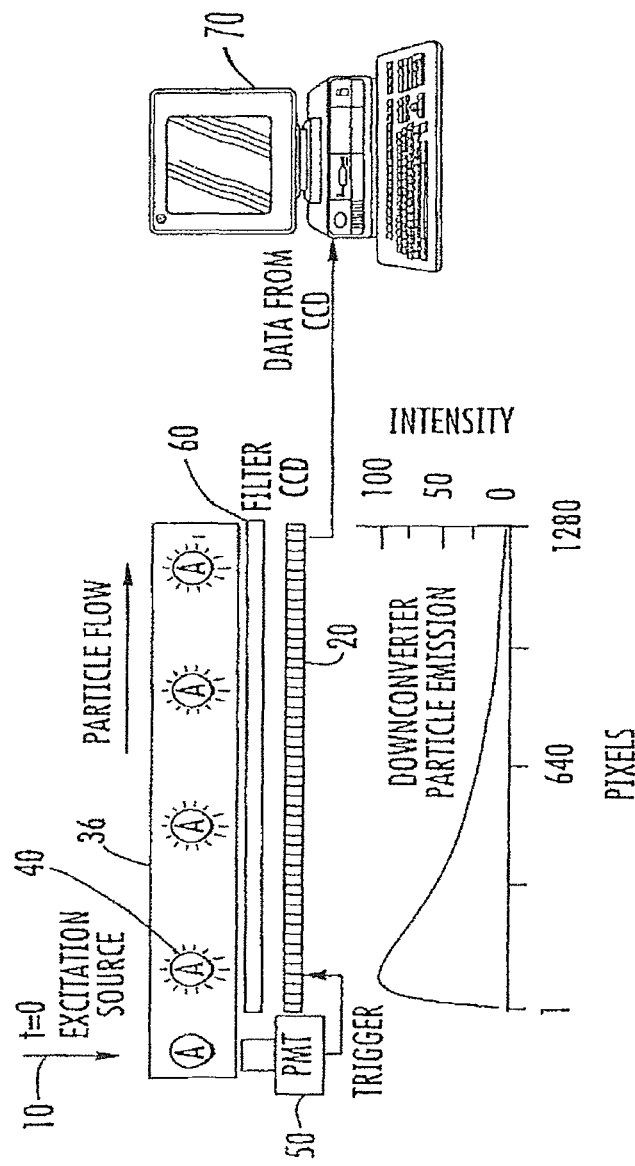
FIG. 2 shows an exemplary embodiment of a flow cytometer apparatus which may be used for rapidly measuring the optical barcodes generated by the rare earth downconverting phosphor composition of the present invention.
Figure 3:
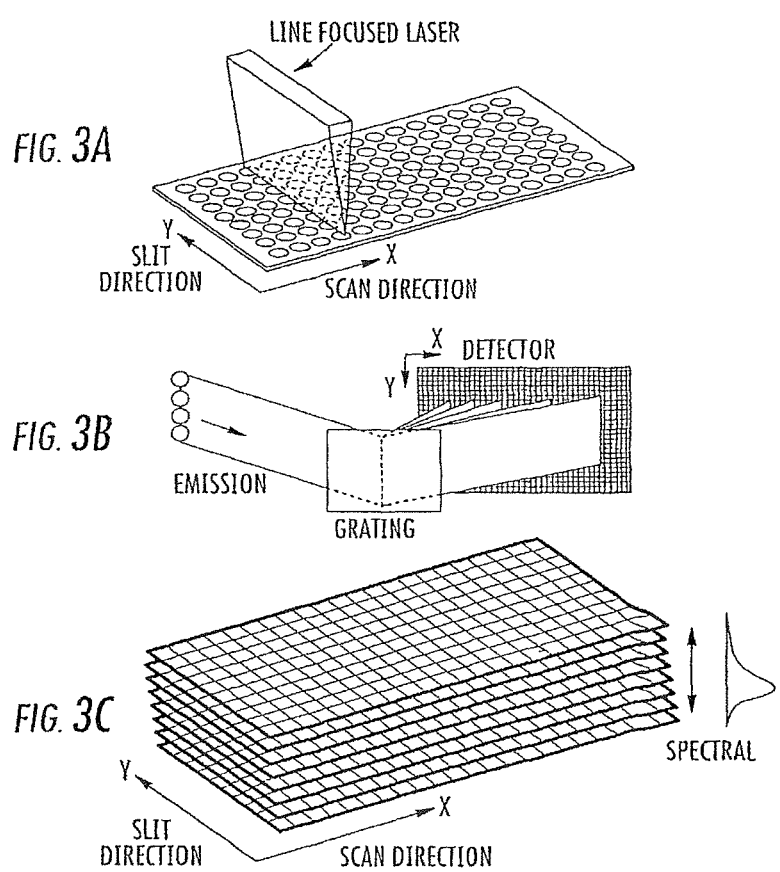
FIGS. 3A-3C depict the operation of an exemplary embodiment of a hyperspectral scanner imaging system, which may be used to read optical signatures or barcodes generated by the rare earth downconverting phosphor compositions of the invention.

Another aspect of the invention is a method by which an optical code (barcode) is generated from the RE downconverter phosphor compositions of the invention, and read (or decoded). Exemplary apparatuses for performing the method are illustrated in FIGS. 2 and 3. The method of the invention uses a ratiometric technique where ratios of the emission intensities are determined as opposed to measuring the absolute intensities of the various emitters. Although there are substantially fewer unique ratios of intensities than there are number of absolute intensities available for the same number of emitters measured at the same resolution, the ratiometric method is more desirable than the absolute intensity method. This is because factors such as, optical geometry, reflectivity of the sample, light scattering within the sample, size and shape of the object, object thickness versus penetration depth of the excitation radiation and the power level of the laser, make absolute intensity measurement difficult. As those skilled in the art will appreciate, if it were possible to measure absolute intensities with the same degree of accuracy and precision as the ratios of emission intensities, then either the ratiometric or absolute intensity methods could be used to create and read the optical codes.

As mentioned earlier with respect to the downconverting composition aspect of the invention, the host lattice itself may function as the absorber of the excitation radiation. The host, which is sometimes referred to as the host lattice, comprises a parent structure or structure type into which the one or more emitters and, if necessary, an absorber are incorporated, generally in the form of a solid solution. The solid solution, in turn, comprises a lattice into which different chemical constituents may substitute randomly and isomorphously into the parent host lattice. In one exemplary embodiment, the RE downconverting phosphor composition may comprise $Y_{1-x}[(RE_1)_a(RE_2)_b(RE_n)]_xVO_4$, where $RE_n$ is one or more of the RE downconverting emitters such as $Ce^{3+}$, $Sm^{3+}$, $Eu^{3+}$, $Gd^{3+}$, $Tb^{3+}$, $Er^{3+}$, $Ho^{3+}$, $Tm^{3+}$, $Pr^{3+}$, $Nd^{3+}$, and $Dy^{3+}$. In this illustrative embodiment, $YVO_4$ comprises the host material and also functions as the absorber, and RE comprises the rare earth emitter. In other embodiments, the RE downconverting phosphor composition may comprise other host materials (and absorbers if required) and at least one emitter. The rare earth emitter concentration substituted into the host lattice may range from about $10^{-4}\%$ to about 10% and preferably between about 0.01% to about 1%.

In some embodiments, the RE downconverting phosphor composition may be combined with other phosphor materials such as IR upconverting phosphors, fluorescent dyes or quantum dots to increase the number of available codes.

The host of the RE downconverting phosphor composition may comprise, without limitation, oxides, oxysulfides, halides, silicates, phosphates, vanadates and oxyhalides, aluminates, tungstates, niobates, oxynitrides or combinations thereof for the above materials. Examples of such host materials may include sodium yttrium oxide, barium or magnesium aluminate, yttrium phosphate, yttrium vanadate, lanthanum oxide, gadolinium oxide, sodium yttrium fluoride, lanthanum fluoride, lanthanum oxysulfide, yttrium oxysulfide, yttrium fluoride, yttrium gallate, yttrium aluminum garnet, gadolinium fluoride, barium yttrium fluoride, and gadolinium oxysulfide.

The dyes that may be optionally combined with the RE downconverting phosphor composition, may comprise fluorescent organic dye molecules. Examples of such dyes may include, without limitation, rhodamines, cyanines, xanthenes, acridines, oxazines, porphyrins, and phthalocyanines and combinations thereof.

The earlier mentioned quantum dots that may be optionally combined with the RE downconverting phosphor composition, are semiconductor crystals of a few nanometers in size (nanocrystals). The nanocrystals may be composed of periodic group II-IV, III-V, or IV-VI materials and may range in diameter from 2-10 nanometers or roughly the size of 10 to 50 atoms in diameter. Typically, quantum dot cores are composed of cadmium sulfide (CdS), cadmium selenide (CdSe), lead selenide (PbSe) or cadmium telluride (CdTe). The quantum dots are often coated with one or more various coatings to increase their solubility, dispersability and provide a layer to which other materials, such as a material to be analyzed like a biomolecule, may be attached. The semiconductor material used for a particular size core is selected based upon the emission wavelength range being targeted: CdS for UV-blue, CdSe for the bulk of the visible spectrum, CdTe for the far red and near-infrared. These cores may be synthesized as nano-sized ($10^{-9}$ meter) spheres, rods, pyramids, boomerangs, tetrapods, and many other shapes. Typically, the quantum dots possess a spherical or slightly elongated ellipsoidal (rod-like) geometry.

In a further aspect of the invention, the encoded RE downconverting phosphor composition is prepared by physically mixing multiple samples of different RE downconverting phosphor compositions to form a multicomponent solid or prepared in situ within one or more particles. Preparation within one or more particles may be performed in any suitable type of particle, a porous glass microsphere (bead) being one preferred type of particle, because it is capable of readily imbibing an aqueous solution. A preferred method for preparing the composition of the invention within a porous glass bead comprises impregnating the pores of the glass bead with a solution comprised of at least one type and amount of soluble host and lanthanide compound precursor of a desired composition, followed by dehydration and thermolysis, and annealing if required, of the soluble precursor into a solid state material. In one exemplary embodiment, the porous glass bead may comprise a Controlled Pore Glass (CPG), which is commercially available with a large surface area and relatively monodisperse pore diameters ranging from about 50-300 nm, specific pores volumes of around 1 mL/gram and a surface area of about 10 $m^2$/gram, which enable it to readily imbibe an aqueous solution. In one exemplary embodiment, the RE downconverting phosphor composition may be prepared from aqueous solutions containing the correct molar ratios of cationic precursor for the host, the one or more absorbers, if needed, and the one or more emitters.

In one exemplary embodiment, the soluble precursor thermolysis method mentioned above may be used to in situ prepare $Y_{1-x}(RE)_xVO_4$, inside porous glass beads by thermally decomposing yttrium nitrate, vanadyl sulfate and an appropriate RE nitrate to produce RE doped yttrium vanadate. More specifically, an aqueous solution containing $Y(NO_3)_3$, $VO(SO_4)$ and at least one emitter in the form of $RE(NO_3)_3$ is prepared and then imbibed by the porous glass beads. The water in the imbibed solution is removed by freeze drying, heating, evaporation or a combination of these methods. The glass beads with the precursors within their pores are then heated slowly to about 600-800° C. in flowing air in order to decompose the nitrates and sulfates to produce doped yttrium vanadate and sulfur and nitrogen oxides and to increase the crystallinity of the products. Since the constituent components are atomically mixed in solution, and there is no plausible demixing mechanism because of the close chemical similarity of the cations of the rare earth emitters, the glass beads will identically reflect the solution concentration ratios of the constituents.

In addition to the precursor imbibition/thermolysis method described above, the downconverting phosphor composition may also be formed within a particle by imbibing a colloidal dispersion of a preformed downconverting phosphor composition into a particle.

Another preferred method for preparing the RE downconverting phosphor composition of the present invention comprises a spray drying and pyrolysis method. In accordance with this method, solutions of the precursors, such as described above, for the host, the absorber, if needed, and at least one emitter are prepared. The solutions then are nebulized into fine droplets, which are in the range of about 0.1 to about 10 microns in diameter and carried with a gas stream into a region of sufficiently high temperature to create a solid state material of interest. In one exemplary embodiment, nebulization may be performed with an ultrasonic nebulizer. The final size of the composition particles obtained after thermolysis can be controlled by the concentration of the precursor solution.

Yet another preferred method for preparing the RE downconverting phosphor compositions of the present invention comprises a flame spray pyrolysis method. In accordance with this method, solutions of the precursors, such as described above, for the host, the absorber, if needed, and at least one emitter are prepared as described earlier, but instead of using nitrates or sulfates in aqueous solution, precursors in the form of their acetonylacetonate or alkoxide complexes are used. These precursors are dissolved in an organic solvent. The organic solvent containing the dissolved precursors is mixed with $O_2$ or $O_2/H_2$ in a torch and burned to the desired solid state material. This method is similar to well known methods for commercially manufacturing flame spray silica.

Still another preferred method for preparing the downconverting compositions of the present invention comprises a combustion synthesis method. In accordance with this method, a desired downconverting composition such as, $(Y_{0.99} Ho_{0.01})_2O_2S$, may be prepared by the mixing appropriate molar ratios of anhydrous Y and Ho nitrates with dithiooxamide $(CSNH_2)_2$. The mixture is then heated to an ignition point whereupon an ensuing deflagrative combustion reaction occurs and forms the desired oxysulfide the solid state material of interest.

Still another preferred method for preparing the downconverting compositions of the present invention comprises a physical vapor deposition (PVD) method. In accordance with this method, a desired downconverting composition is deposited onto an object or sample to be encoded, as a series of layers using PVD. PVD may be performed using pulsed laser deposition, sputtering, e-beam, or thermal evaporation.

Yet another preferred method for preparing downconverting compositions of the present invention comprises reacting appropriate amounts of constituent binary oxides. For example, an $Eu^{3+}$ doped yttrium vanadate material may be prepared by mixing finely divided $Y_2O_3$ and $V_2O_5$ with the appropriate amount of europium nitrate in ethanol in a ball mill for 24 hours. After complete evaporation of the ethanol, the sample is heated for 10 hours at 1300° C. The heating and grinding steps are repeated several more times until the reaction is complete.

Another aspect of the invention comprises the use of the RE downconverting phosphor compositions to encode a variety of samples or objects. Such samples or objects may include, without limitation, paper documents, optical media, automobile components, humans or animals, food packaging, pharmaceutical preparations, and biological samples. Where a paper document is encoded, the document may be impregnated with a colloidal dispersion of a desired RE downconverting phosphor composition of the invention. Impregnation may be performed, for example, by a printing, dipping or spraying process or by mixing the desired downconverting phosphor composition with the paper pulp during manufacture. Any of the above objects may be treated with a paint, ink or pigment that contains one or more desired RE downconverting phosphor compositions of the invention. Objects can also be encoded by affixing a piece of adhesive backed material containing one or more desired RE downconverting phosphor compositions onto the object to be encoded. Optical media may be encoded, in one exemplary embodiment, by casting a desired RE downconverting phosphor composition directly into the polymer used to make the optical media.

Biological samples may be encoded, in one exemplary embodiment, by incorporating particles containing one or more desired RE downconverting phosphor compositions into the sample. For example, a nanoparticle (about 10 nm in size) of a desired RE downconverting phosphor composition may have an antibody attached to its surface. When the antibody is exposed to its appropriate receptor or target within in a cell, it binds to it and optically encodes that receptor or target. Many cell parts, chemicals and structures may be visualized and optically encoded simultaneously to determine their identities because of the large number of codes available using the present invention. In an alternate exemplary embodiment, biological molecules may be attached to particles of a desired RE downconverting phosphor composition of the invention or to particles that contain a desired RE downconverting phosphor composition of the invention. The biological sample may comprise any type of biomolecule, without limitation, with DNA, RNA and proteins comprising particularly preferred biological samples. Where the particles are a composition containing glass beads (as described earlier), or materials with surface hydroxyl X—OH functionalities, DNA may be attached to each particle through a series of steps. For example, in one exemplary embodiment, trisethoxy-n-propylsilylamine may be reacted with the Si—OH groups of the surface of the glass bead. Protonation of the aminated surface generates a polycationic substrate. Addition of polyanionic DNA to the substrate results in attachment through a series of ionic bonds. The multiple ionic bonds ensure that the attachment can withstand a variety of mechanical and solvent-induced forces.

In another exemplary embodiment, the biological molecules (e.g., DNA, RNA proteins and polypeptides) may be attached to a desired RE downconverting phosphor composition of the present invention through a series of chemical reactions which attach the biological molecules to the composition through covalent bonds. For example, a protein may be attached to a particle containing a desired RE downconverting phosphor composition, by coating the particle with silica, mixing the particle with a solution of tetraethoxysilane (TEOS), $Si(OCH_2CH_3)_4$, and subjecting this mixture to hydrolysis to hydrolyze the TEOS to $SiO_2$. Next, the silica surface of the particle is aminated as above and crosslinked to the protein with, for example, glutaraldehyde.

A further aspect of the invention comprises the use of one or more RE downconverting phosphor compositions in a method for sample detection and identification by excitation of the RE downconverter phosphor compositions. As described earlier, the two or more downconverting emitters in the composition, either in the form of two or more different emitters in at least one host, or a mixture of two or more individual phases containing one or more emitters in each phase, absorb photons at a particular wavelength and subsequently emit electromagnetic energy at an emission wavelength higher, or lower energy, than the excitation wavelength. In accordance with this aspect of the invention, the intensity of the each excited downconverter emitter's emission is measured, and the ratios of the intensities are calculated. The emission intensity is proportional to the amount of encoding material present assuming that there is weak or no interactions among any emitters or particles. One or more of these ratios constitute a code that distinctly and uniquely identifies the sample.

The sample detection and identification method may be further illustrated by way of a description of a RE downconverting phosphor composition comprising two downconverting emitters A and B with each of the two emitters displaying five distinguishable emission intensities. If each emission intensity is given a designation of 1, 2, 3, 4 or 5, then twenty-five different combinations can result from the two downconverting emitters, as shown below in Table 1.

TABLE 1

| | | Emission intensity of A | | | | |
|---|---|---|---|---|---|---|
| | | 1 | 2 | 3 | 4 | 5 |
| Emission intensity of B | 1 | 1, 1 | 1, 2 | 1, 3 | 1, 4 | 1, 5 |
| | 2 | 2, 1 | 2, 2 | 2, 3 | 2, 4 | 2, 5 |
| | 3 | 3, 1 | 3, 2 | 3, 3 | 3, 4 | 3, 5 |
| | 4 | 4, 1 | 4, 2 | 4, 3 | 4, 4 | 4, 5 |
| | 5 | 5, 1 | 5, 2 | 5, 3 | 5, 4 | 5, 5 |

Assuming that each cell of Table 1 represents a sample with a corresponding RE downconverter phosphor composition, one can measure intensity at different emission wavelengths, take the ratio of the intensities of the different wavelengths, and distinguish (i.e., read the code of) the samples from one another in two different ways by using absolute or ratiometric intensity methods.

If one can measure the absolute intensity at the two emission wavelengths, then the code "1,1" can be distinguished from "3,3," for instance and therefore all of the 25 compositions in Table 1 can be distinguished using the absolute intensities. In contrast, when employing the ratiometric method, only five different ratios may be obtained and the number of resolvable codes or identifiable samples is reduced by a factor of five. The ratiometric method has several advantages over absolute method as described earlier. The number of codes of course can be increased by adding additional emitters or resolving the original codes at a higher level.

In one exemplary embodiment, wherein the RE downconverting phosphor composition comprises a binary mixture of lanthanide materials A and B, emission intensities can be distinguished using the ratiometric method described above, which drastically decreases the number of available codes as compared to measuring the absolute intensity ratios. More specifically, if the binary mixture of lanthanide materials A and B is designated $A_xB_{x-1}$ where x is a value between 0 and 1, ratios can be optically differentiated at intervals of less than 0.3% at a 2σ confidence level. This means that greater than 300 separate ratios (codes) can be detected and resolved within the two downconverting A-B lanthanide material system. In another exemplary embodiment wherein the RE downconverting phosphor composition comprises a ternary mixture of downconverting lanthanide materials having different emission wavelengths, about 90,000 resolvable codes or samples can be distinguished within the ternary downconverting lanthanide material system. In still a further exemplary embodiment wherein the RE downconverting phosphor composition comprises a quaternary mixture, such a composition allows the identification of about $2.7 \times 10^7$ samples or resolvable codes. In yet another exemplary embodiment wherein the RE downconverting phosphor composition comprises a quintary mixture, this composition provides for the identification of $8.1 \times 10^9$ samples or resolvable codes.

The number of resolvable codes or identifiable samples derived from a certain number of different RE downconverting phosphor compositions may be increased by combining additional species (e.g, the earlier described dyes and quantum dots), which can undergo excitation and subsequent emission of light, that do not contain downconverting compositions themselves. The presence or absence of a single fluorescent dye, for example, to a mixture of downconverting composition containing samples doubles the number of identifiable samples.

Sample or object detection and code-reading using the RE downconverter phosphor compositions may be generally performed in a series of steps. In one exemplary embodiment, a sample or object combined with a RE downconverting phosphor composition is illuminated with electromagnetic radiation at a wavelength suitable to induce excitation. If the composition contains at least two downconverting emitters, the sample or object is typically excited using radiation of about 200 nm to about 450 nm, and preferably 230 nm to 375 nm. For a sample possessing a $YVO_4$ host, the 325 nm output of a He—Cd laser is a preferred illumination/excitation source. Second, radiation at two or more emission wavelength bands is detected by a detector from the at least two emitters. The excited downconverting composition, in one embodiment, may emit radiation in the 350 nm to 850 nm range, most of which is within the visible range. The intensities of the emitted radiation is then used to calculate at least one ratio of emission intensities. The obtained ratio provides a unique code if the intensities are known.

Alternatively, one may compare the obtained ratio to an internal standard, which provides the unique set of codes. Using a binary color A and B as an example, if the absolute intensities can be measured with sufficient accuracy, then ratios such as 1:1, 2:2, 3:3, . . . n:n would may be resolvable. However, when the data is analyzed ratiometrically all of these ratios are degenerate and not resolvable from one another.

The excitation source used in the sample or object detection and code-reading method described above may include laser diodes, arcs, and discharges of any type of incandescent filament. Deuterium and mercury discharge lamps are also good excitation sources. It is also possible to use wavelengths emanating from the sun. As stated above, the 325 nm output of a He—Cd laser is particularly convenient excitation source for suitably absorbing hosts such as $YVO_4$. Undesirable wavelengths from the source illumination may be filtered from the detector using optical filters that have low transmissibility for the excitation wavelength. The excitation illumination may also be multiplexed and/or collimated, for example through the use of a dichroic mirror array. This would allow the simultaneous excitation of multiple downconverter species having different excitation wavelength bands. The illumination may be continuous or pulsed or a combination of the two. Such a combination would allow signal discrimination between continuous wave induced and pulsed phosphorescence. One may then discriminate between multiple phosphor species having similar emission spectra but different excitation spectra.

Pulsed radiation of sufficiently short duration, where the pulse is much shorter than the lifetime of the species to be excited and read, can be used to time resolve organic dye emitters (excited state lifetimes of about nanoseconds) from any organic dyes or quantum dots used in conjunction with the RE downconverting phosphor compositions (lifetimes generally in the 0.1 millisecond time range).

The emitted radiation from excited downconverting emitters in the RE phosphor composition can be detected and quantified in a number of ways using visible absorption spectroscopy. The detector may include, without limitation, photomultiplier tubes (PMTs), avalanche photodiodes, charge-coupled devices (CCD), charge-injection devices (CID), or arrays of these devices, photographic film emulsion, photochemical reactions yielding detectable products, and visual observation (e.g., fluorescent light microscopy). Residual background noise in the detected emissions may be decreased through the use of time-gated and/or frequency-gated light collection. Rare earth downconverting phosphor compositions typically have emission lifetimes on the order of a few milliseconds, which is in contrast to the 100 ns decay of background noise. This makes the use of time-gated detection desirable when using a pulsed excitation source.

Where the downconverting compositions are used to encode samples of a biological assay, excitation, detection and quantification may be performed in one exemplary embodiment, using a Flow Cytometer. Flow Cytometers (FC) have been used in conjunction with downconverting phosphor materials, as described in US published Pat. Appl. 20030207331; U.S. Pat. No. 6,537,829; U.S. Pat. No. 6,399,397; U.S. Pat. No. 6,159,686; U.S. Pat. No. 5,891,656; U.S. Pat. No. 5,674,698; and U.S. Pat. No. 5,698,397; the disclosures of which are incorporated herein by reference.

For certain applications, such as gene expression or genotyping, high sample throughput using a flow cytometer depends not only on the quality and multiplexing depth of the encoding system; it also depends on the method optically evaluate particles very rapidly. In order for the system to display maximum utility, the encoding system must interfere with as few preexisting, standard assays as possible. For gene expression in particular, the encoding system cannot interfere with conventional cy3/cy5 organic dye combinations or their optical equivalents, which is used to determine the sample and control DNA ratios in hybridization experiments. This can be problematic as there is a great deal of spectral overlap between the RE downconverting phosphor compositions and the cy3/cy5 emitters.

The above-described problem can be overcome by taking advantage of the large difference in excited state lifetimes of the RE downconverting phosphor compositions and organic emitters. This may be accomplished in the present invention, by temporally resolving two emission types by either using a detector fast enough to resolve the emission from the organic and RE species or the rapid flow inherent in the flow cytometer, or both. By judicious selection of the particle size, flow rate, length of detection region and detector rise time, resolution and frame rate, many "snapshots" of the encoded particles moving past pixels of a CCD detector can be obtained and the intensity summed from each pixel to measure the entire emission profile. The temporal resolution scheme may be predicated on typical organic emitters having excited state lifetimes of 1-10 ns, while the rare earth downconverting phosphor compositions emitters have much longer characteristic corresponding lifetimes of ~10 ms for $Er^{3+}$, ~2 ms for $Yb^{3+}$, ~1 ms for $Eu^{3+}$, ~0.1 ms for $Dy^{3+}$, ~0.3 ms for $Tb^{3+}$, for example. These lifetimes are directly related to emission peak width and this is what allows the rare earth downconverting compositions of the present invention with narrow emission bands to be multiplexed so deeply and why organic based emission is very broad by comparison.

FIG. 2 shows an exemplary embodiment of a flow cytometer apparatus according to the present invention for very rapidly measuring optical barcodes generated by the RE downconverting phosphor compositions of the invention. The flow cytometer (FC) comprises one or more excitation sources 10, a linear CCD detector 20 and a flowing stream of fluid 30 (such as water, buffers or air) for entraining the particles 40 to be analyzed and moving them past the detector 20 at a fast rate, for example, 1-10 m/s. The flow cytometer further comprises a PMT 50 for detecting the promptly emitted light from an organic dye or quantum dot and an optical filter 60 disposed downstream from the PMT 50 and lateral to the CCD detector 20. The optical filter 60 removes undesirable wavelengths in the source illumination so that they are not detected by the CCD detector 20. A computer 70 is provided for processing the emission intensity data. The encoded beads 40 are moved in relation to the detector 20 by entrainment in the internal flow system of the flow cytometer which uses the liquid or gas stream 30 to move the particles 40. In accordance with the present invention, the FC flow rate may be adjusted to the decay time of the encoded object 40, emission intensity and the pixel size and number of pixels in the detector 20.

Based on this, the flow rate is increased to allow more beads to pass through the optical field of the CCD per second. Each frame triggered by PMT digitizes all emission intensities of all beads which are in the view of CCD during the exposure time. The exposure time is the dwell time of each bead before each pixel of the CCD. The sampling rate is the frame rate. All frame data is transferred to the computer and is analyzed to show the emission in real-time.

In one exemplary embodiment, the beads may travel at a speed of 10 $ms^{-1}$ labeled with $Er^{3+}$, which has the longest decay time (1 ms) of any of the RE ions used, and the linear CCD may comprise 1028 pixels. In this embodiment, each bead stays at one pixel for 7.8 μs, which is the exposure time. The interframe time is set to 100 ns. Therefore 1280 beads with a interparticle spacing of 78 μm are resolvable in one frame. If the frame rate is 128 Kfps, then 128,000 beads are counted in one second. This data volume equals one frame of an area CCD with 1280×1024 pixels. It is therefore possible to resolve and detect $8 \times 10^7$ beads in one second. Beads with a shorter excited state lifetime can be read even faster.

It should be understood that other detection schemes are possible in addition to those making use of a flow cytometer. In another embodiment the multicolor emission from the encoded particles is detected, measured and analyzed using a hyperspectral imaging system. The operation of an exemplary embodiment of a hyperspectral imaging system to image the encoded particles is illustrated in FIG. 3A-3C. The hyperspectral imaging system measures the emission spectrum for each pixel in an image. As shown in FIGS. 3A-3C, a "data cube" is generated with the slit orientation, and the direction of slide scanning and emission spectra make up the three axes of the data cube. Hyperspectral imaging has been used previously to measure spots on a microarray slides and other objects.

In an exemplary embodiment, the hyperspectral imaging system and beads encoded with the RE downconverting phosphor materials compositions of the invention, may be used in an experiment to determine gene expression. The information obtained from this experiment, which is the expression level of a given gene represented by the single strand of probe DNA, is very similar to that of a traditional gene expression slide-based microarray experiment. The beads impregnated with the RE downconverting phosphor compositions so as to generate an optical code (e.g. doped yttrium vanadate impregnated CPG particles) have different single strands of DNA attached to each differently barcoded bead. The barcoded DNA probes are combined in a flask and hybridized with the desired targets en masse up to millions or billions at a time. After the hybridization is complete, employing, for example, a common combination of cy3 and cy5 labeled probe DNA samples to determine the relative amounts of sample and control targets bound to the probe, all of the particles are scanned in the hyperspectral imaging system. For example, in particle samples of encoded $Y_{1-x}(RE_n)_xVO_4$, the visible output of the optical barcode is read from the particles using the 325 nm excitation from a He—Cd laser which is a wavelength that does not efficiently excite the cy3 or cy5 dyes. Next the samples are sequentially scanned with 532 nm and 632 nm lasers to measure the amount of cy3 and cy5 dyes, respectively, present in the samples. Using these sequences of excitation and detection, the sample is identified from its barcode and then the amount of over or under expression of a particular sample is determined from the cy3/cy5 ratio.

EXAMPLES

The following examples illustrate how the emission from the downconverting compositions can provide the desired degree of multiplexing for a wide variety of applications. In certain exemplary embodiments disclosed herein, the host or host lattice also functions as the absorber of the excitation radiation and various other trivalent rare earth ($RE^{3+}$) cations such as $Tm^{3+}$, $Pr^{3+}$, $Ho^{3+}$, $Dy^{3+}$, $Er^{3+}$, $Eu^{3+}$, $Ce^{3+}$, $Nd^{3+}$, $Sm^{3+}$ and $Tb^{3+}$ comprise the emitter within the downconverting composition. In the downconverting composition $Y_{1-x}(RE)_xVO_4$, $YVO_4$ serves as both the host lattice and absorber.

It will be understood by those skilled in the art that in addition to the examples disclosed here, there are a very large number of other types of objects or samples that can be encoded, other combinations of reporters to combine with the RE downconverting phosphor compositions and other rare earth absorbers and emitters that can be used in a fashion similar to the exemplary embodiments disclosed here. The following examples are provided to illustrate the principles of the invention and are not meant to limit the scope of the invention in any manner.

Example 1

A Rare Earth Downconverting Phosphor Composition Comprising Two or More Lanthanide Materials, Wherein Each Lanthanide Material Comprises a Host and One or More Emitters Example 1 demonstrates how intensity ratio measurements within a series of variable emitter downconverting compositions materials can provide the desired degree of multiplexing for encoding very large numbers of objects. The results of this experiment demonstrate how a mixture or mixtures of the various downconverting compositions can be optically resolved and how the optical resolution was determined.

The host materials fabricated for this example of the RE downconverting phosphor composition are comprised of $YVO_4$, which can contain the rare earth emitters $Tm^+$, $Pr^{3+}$, $Ho^{3+}$, $Dy^{3+}$, $Er^{3+}$, $Eu^{3+}$, $Ce^{3+}$, $Nd^{3+}$, $Sm^{3+}$ and $Tb^{3+}$ and preferably $Tm^+$, $Ho^{3+}$, $Dy^{3+}$, $Er^{3+}$, $Eu^{3+}$ and $Sm^{3+}$. For the studies to establish the compositional resolution that could be optically determined, physical mixtures of standards were prepared from bulk single emitter solid state samples of $Y_{1-x}(RE)_xVO_4$ with $RE=Dy^{3+}$, $Er^{3+}$, $Eu^{3+}$, $Ho^{3+}$, $Sm^{3+}$ and $Tm^{+3}$. In this case the $YVO_4$ host lattice also functions as the absorber for the 325 nm excitation radiation from a He—Cd. These compounds were weighed together in the appropriate ratios and thoroughly mixed. The ratios were obtained by integrating the appropriate spectral regions for the two emitters and calculating the emission ratio for each mole or weight ratio.

Figure 4:
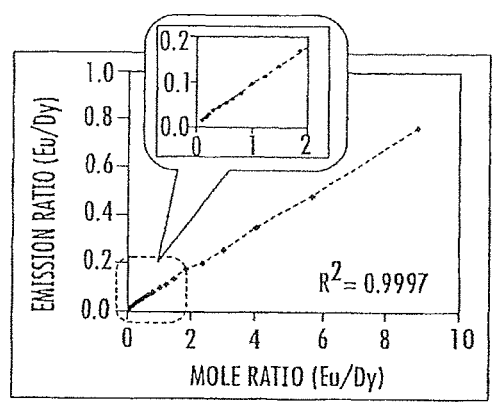
FIG. 4 is a graph illustrating a decoding or calibration plot which shows the linear relationship between emission ratio and mole ratio of a binary library of Eu and Dy doped $YVO_4$ samples ranging from 10% to 90% with 5% increment levels.
Figure 5A:
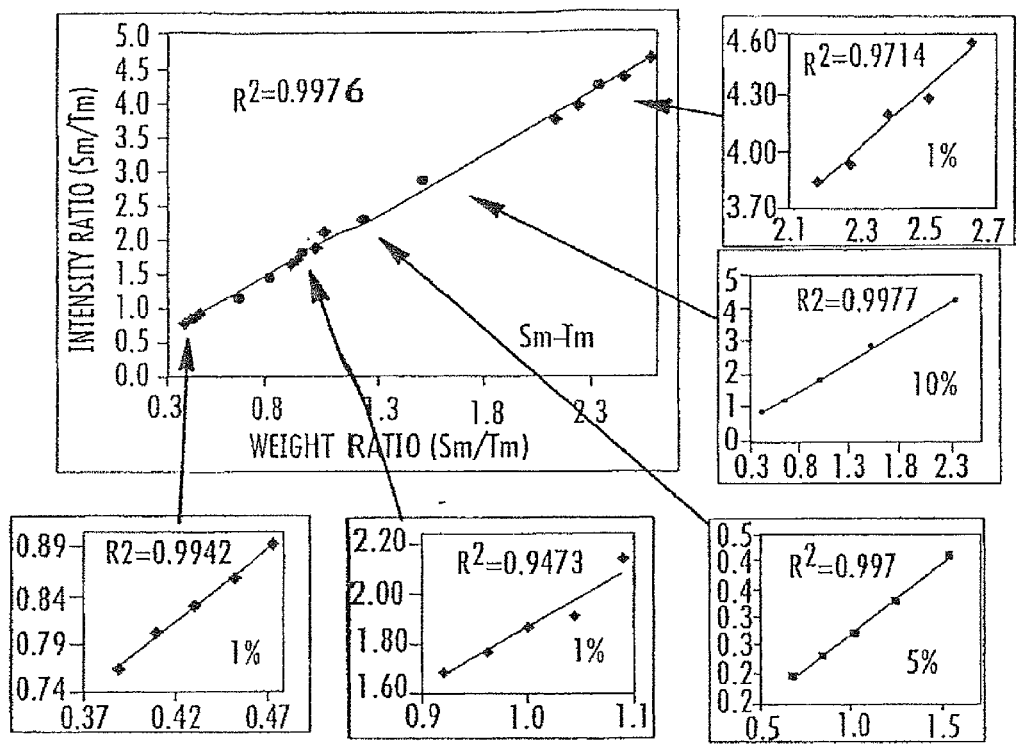
FIGS. 5A-5E are graphs illustrating calibration plots of samples of $YVO_4$-based rare earth downconverting phosphor compositions of the invention, which may be used in a decoding process of the invention.
Figure 5B:
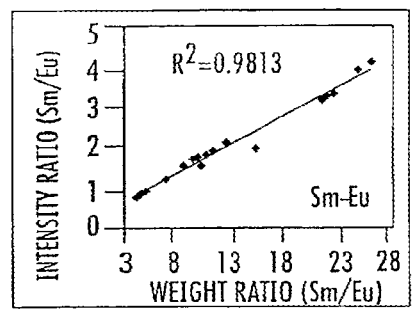
Figure 5C:
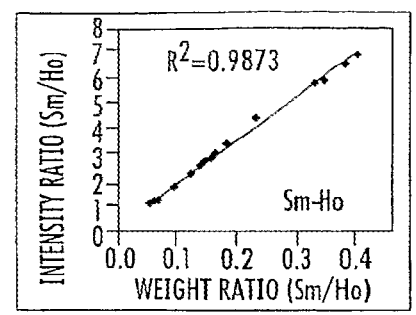
Figure 5D:
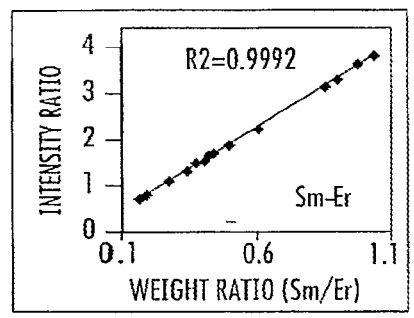
Figure 5E:
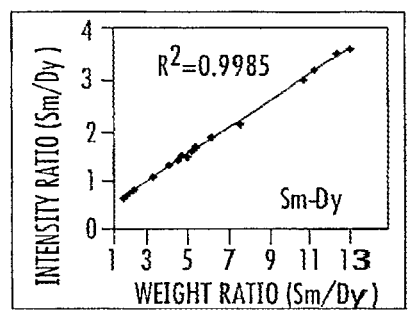

The compositional dependence of the integrated intensities of selected regions of the Eu and Dy emitter spectra are shown in FIG. 4 for these samples. Integrated intensity data points were obtained by selecting the wavelength range for each emitter within which the integration will be performed and counting the number of photons impinging on the detector during a certain time period. It is clear that there is a linear relationship between the ratios of the integrated intensity of the two emitters and the ratio of the amounts of the two emitters present (FIG. 4) and when one is known the other can be determined. From the physical mixtures of the lanthanide materials made from RE doped $YVO_4$, relative ratios of two emitters can generally be determined at the 1% resolution level. If the six emitters $Tm^+$, $Ho^{3+}$, $Dy^{3+}$, $Er^{3+}$, $Eu^{3+}$ and $Sm^{3+}$ doped into the $YVO_4$ host, or physical mixtures of the six pure single emitter compounds, can be resolved at the 1% level, then there are $10^{10}$ resolvable codes available for use in sample or object labeling in this system when using the ratiometric analysis.

Example 2

A Rare Earth Downconverting Phosphor Composition Comprising Two or More Rare Earth Emitters within One Host Phase In the following examples, samples were measured by illuminating the with the 200-345 nm output from a high pressure Hg arc lamp or the 325 nm output from a He—Cd laser and collecting the emitted light in the 350-850 nm range with a fiber coupled spectrometer.

In this example, an optical barcode based on doped samples $Y_{1-x}(Eu_aEr_b)_xVO_4$, with x=0.01 and a+b=x may be prepared with the yttrium site in the host lattice partially substituted with Eu and/or Er. In this case $YVO_4$ is the host lattice, host or host material, the $YVO_4$ host lattice is the absorber of the UV photons (ultraviolet), including nearby wavelengths as well, and Eu and Er are the emitters of the visible photons. A series of RE downconverting phosphor compositions may be prepared containing many Eu/Er ratios within a single host lattice. One such composition may be $Y_{1-x}(Eu_{0.005}Er_{0.005})_xVO_4$ and another in the series of compositions may be $Y_{1-x}(Eu_{0.006}Er_{0.004})_xVO_4$. To prepare this particular sample, a mixture of $Y_2O_3$, $V_2O_5$ and the appropriate amounts of the nitrates of Er and Eu are thoroughly ground together with ethanol for several hours in a ball mill. After complete evaporation of the ethanol the sample is heated to 1300° C. for several hours. The samples are ground again and reheated until the reaction is complete. Alternatively the materials can be prepared by one of the solution thermolysis methods discussed above. It will be understood by those skilled in the art that there are many other ratios, in addition to the two ratios demonstrated here, which may be used to identify a particular sample. The number of samples which may be distinguished using a ratio of two components depends on the resolution, accuracy and repeatability of the technique used to measure the ratio. Additional rare earth cations may be added to further increase the number of individual samples that may be encoded; for example, three components, may be incorporated, as in $Y_{1-x}(Eu_{0.005}Er_{0.004}Dy_{0.001})_xVO_4$, to further increase the number of samples that may be encoded. It is clear to those skilled in the art that many other rare earth emitters in many varying ratios lay within the scope of this type of material.

Example 3

Compositions Comprising More than One Rare Earth Emitter within More than One Host Phase A ratio of two or more lanthanide materials, each comprising a different, single rare earth emitter within a host material, may also be prepared. While the rare earth emitters must be different in order to create a ratio of two emitting species, the host materials in which the individual emitters reside may be the same or different host materials. An example of this type of barcode is a physical mixture of $Y_{1-x}(Eu_aEr_b)_xVO_4$ and $Y_{1-x}(Ho_aDy_b)_xVO_4$ in varying ratios to give a series of codes. By adjusting the amounts of the two materials any arbitrary ratio may be prepared. It is also clear that three or more components can be added to each material to further increase the number of samples that can be encoded by this method. An example of this type of three emitter barcode would be a physical mixture of $(Y_{0.97}Er_{0.01}Eu_{0.01}Dy_{0.01})_2O_3$ and $(Y_{0.98}Ho_{0.01}Sm_{0.005}Tm_{0.005})_2O_2S$.

Example 4

Combination of Visible or Infrared Excited Phosphors, Dyes or Quantum Dots with the Downconverting Composition Materials The degree of sample multiplexing can be further increased by using another absorber/emitter in combination with the RE downconverting phosphor composition to encode samples. For example, if samples were encoded with an organic dye that is excited at 500 nm and emits at 600 nm and since there is no emission from the downconverting composition materials upon excitation with visible wavelengths such as 500 nm, the number of individual barcodes for a group of samples increases by a factor of two based on whether the organic dye is present or absent. If a resolution higher than present or absent can be obtained with the dye, then additional levels of multiplexing could be accessed and even more samples or objects distinguished. Another example would be the use of an upconverting phosphor, such as $(Y_{0.8}Yb_{0.17}(RE)_{0.03})_2O_2S$ with RE=Tm, Er, Ho, or Pr which, when excited with infrared of about 980 nm, emits into the visible. When combined with the aforementioned RE downconverting phosphor compositions a larger number of samples could be distinguished than by the use of either the upconverting or downconverting materials individually. Similarly, the use of quantum dot luminescent materials within these formulations would increase the number of distinguishable encoded objects even further. It is evident to those skilled in the art that the optical encoding capabilities of the RE downconverting phosphor compositions can be conveniently combined with the upconverting phosphor compositions as the two phosphors types will not interfere with one another as there is no cross excitation of the two phosphors from the 980 nm and UV excitation radiation. Clearly, if the additional luminescent materials can be distinguished more accurately than simply on and off relative to the RE downconverting phosphor compositions (optical barcodes), the degree of multiplexing increases further still.

Example 5

Preparation of Combinatorial Continuous Gradient Libraries and Measuring Emitter Ratios in a Four Color System: Layered Downconverting Compositions In addition to labeling an object with the RE downconverting phosphor composition in a particle form in order to distinguish, identify, sort or recognize it, objects may be encoded by depositing layers, from any type of deposition source including, without limitation, such sources a sprayers, vaporizers, sublimators, and typical thin film deposition methods. The libraries (a series of related RE downconverting phosphor compositions) are prepared by depositing many thin gradient layers of the appropriate oxides to make the final RE downconverting phosphor compositions.

The libraries are fabricated in a PLD or sputtering apparatus which contains linear motion shutters, a rotating target carousel (PLD) or separate targets (sputtering) and the ability to rotate the substrate about an axis perpendicular to the plane of the substrate. Ultraviolet pulses from a xenon difluoride excimer laser ablate plumes from the targets, of composition very similar to that of the target, which deposit on the substrate after interacting with the shutter and mask. Since the deposition flux is uniform in terms of aerial homogeneity and directionality, and the shutter moves with a precisely linear motion, the composition of the libraries as function of library location is well known.

Four targets, for example, $(Y_{0.99}(RE)_{0.01})VO_4$ with RE=Sm, Dy, Er, and Eu, are placed on the target carousel. The targets may be prepared by grinding $Y_2O_3$ and the appropriate $(RE)_2O_3$ oxide (RE=Sm, Dy, Er, and Eu), firing at 1350° C. overnight and repeating the process three more times to ensure homogeneity. After determining phase purity by XRD the samples are isostatically compacted at 600° C. and ~30 tons pressure to form the PLD or sputtering targets. Shutters are defined here as solid objects while masks contains apertures. A mask with a triangular aperture is placed in between the deposition source and the substrate as the material of interest is deposited. In the absence of a shutter the material deposited on the substrate has a uniform thickness profile. Hence the deposition scheme employed here uses a shutter with x motion placed over a stationary mask and substrate (or vice versa) as shown.

While the deposition of material $Y_{1-x}Eu_xVO_4$ is in progress, the shutter is moved slowly in the x direction until it covers the entire aperture. A deposit with a gradient is formed. Next, the source of deposition is shut off; the shutter is moved back to its initial position in the −x direction, and the substrate is rotated by 120° with respect to an axis perpendicular to the plane of the substrate. The second deposition source $(Y_{1-x}Dy_xVO_4)$ is then started and the shutter is again moved slowly in the x direction. This produces the layers of the two materials in the desired 120° wedge orientation. This process is repeated again for depositing the third material $Y_{1-x}Sm_xVO_4$ giving rise to a ternary library, where the three wedges are oriented 120° with respect to each other. After depositing a suitable number of layers by alternating the three sources each library optically constitutes a ternary phase diagram with respect tot the overall layer composition.

To determine the resolution at which the ratios of the downconverting composition emitters are determined the same well known oxide host with the same emitters, namely $(Y_{0.99}(RE)_{0.01})VO_4$ (RE=Sm, Dy, Eu and Er are used in all cases. First, four continuous ternary phase diagrams are prepared each with three of the four Sm, Dy, Eu and Er emitters to give the four Sm—Dy—Eu, Sm—Eu—Er, Sm—Dy—Er and Dy—Eu—Er ternary libraries. This allows the direct experimental determination of the optical response for an arbitrary ternary ratio mixture in a library as discussed below. Since these libraries can easily be dimensionally expanded (i.e., the same composition gradient spread over a larger area) by simply changing the relative thickness of the deposited layers, any compositional region of the phase diagram can be zoomed and magnified. Therefore, the continuous gradient libraries allow an exact determination of the accuracy to which the ratios can be measured. By measuring the standard deviations on a series of measurements for a given ratio, it is possible to place boundaries on the lowest resolvable limit of the ratio.

The overall standard deviation for a ternary library, $\sigma_{overall-3}$ is calculated from the standard deviations of the constituent binary ratios $\sigma_{overall-3}=[(\sigma A/B)^2+(\sigma A/C)^2+(\sigma B/C)^2]^{1/2}$. The standard deviation for the quaternary library is calculated to be $\sigma_{overall-4}=[(\sigma A/B)^2+(\sigma A/C)^2+(\sigma A/D)^2+(\sigma B/C)^2+(\sigma B/D)^2+(\sigma C/D)^2]^{1/2}$. By measuring the magnitude of $\sigma_{overall-4}$ for each 10% increment in D compositions in the quaternary system, one can determine the level of differentiation for individual 4-color barcodes.

Example 6

Employing Downconverting Phosphor Composition-Based Optical Barcodes to Perform a Gene Expression Experiment A description of using the present embodiments to perform a function similar to that of a DNA microarray is given in this example. One use of a DNA microarray is to monitor gene expression. Currently, the DNA samples in a microarray are in the form of a small spot of DNA (75-150 microns) whose identity is known from its location (address) on the substrate. This is a laborious, sensitive and time consuming procedure to print and process these slides. The slides are probed with two types of DNA (control labeled red and sample labeled green) and the test is evaluated by the ratio of red to green in each sample. The present invention will allow an easier, less expensive, less time consuming and potentially more accurate method to obtain the same information.

This example addresses how to prepare and evaluate a sample containing 10,000 different DNA molecules. The 9999 beads or particles are prepared where each of the four emitters is present in increments of 10%. Thus, each of the four emitters can have ten concentrations values between zero and one in 10% increments corresponding to the ten digits zero through nine sufficient to differentiate the 10,000 samples when using the absolute intensity analysis method. Each could have an identifier (or code) such as 3256, which would correspond to the emitters A, B, C and D in ratio of 3:2:5:6. If the ratiometric method was employed instead of measuring absolute intensities, and the resolution was still 10% (i.e. ten samples resolvable within a binary $A_{1-x}B_x$ mixture for $0 \leq x \leq 1$) then 1000 samples instead of 10,000 would be resolvable for a four emitter system.

Next, 10,000 different beads or particles labeled with the downconverting materials are prepared and 10,000 different single strand oligonucleotides, each corresponding to a particular gene or sequence of interest, are attached to the beads such that a single known oligonucleotide is associated with a single known bead composition. Therefore a given nucleotide can be identified from the optical signature of the particle to bead or particle to which is it attached.

As in the currently performed microarray experiments, the test and control probe DNA are labeled with two different dyes but then the DNA probes are mixed with the rare earth downconverting phosphor composition encoded beads instead of being hybridized to the DNA samples on a slide. Using a bead or cell sorter, a flow cytometer or a device with a similar function, the beads or particles with the desired hybridization behavior are separated and identified and the organic dyes and downconverting phosphor composition emissions are temporally resolved as described above. The oligonucleotides in each of the latter samples are thus identified by the optical signature from their unique downconverting phosphor composition. Therefore which genes or sequences were over or under expressed in the original sample can be determined. The underlying microarray experiment is the same except that the sample is identified by its downconverting phosphor composition optical barcode rather than by its physical location on the microarray slide.

Example 7

Preparation of Downconverting Barcode Materials Based in Controlled Pore Glass (CPG)

A convenient form for the barcode materials of the present invention is a particle based format where the barcode materials are in the form of particles in the size range of 1 nm to 200 microns or more preferred about 10 nm to 100 microns. One current problem in preparing particles of pure downconverting composition materials is that the rare earth oxide host components are often very refractory and the particles tend to aggregate upon treatment at temperatures sufficient to crystallize the host which is necessary for good phosphor efficiency. Many applications for the barcoded materials formed from the downconverting phosphor composition materials require them to be in a particle or bead format especially for highly parallel biological experiments. One very convenient method to accomplish this is to fill the pores of a highly porous material, which has been preformed as a bead or particle, with the RDP material. However, this method is not without problems because the exact chemical nature of the host lattice in which the RE emitter resides has a very strong influence on the wavelength and efficiency of the emitted light. For instance when rare earth downconverting materials are prepared in a silicon dioxide ($SiO_2$) host material, the number of colors and the efficiency of the emitters is relatively low. However, barcoded particles can be conveniently prepared on a $SiO_2$ matrix by employing controlled pore glass (CPG). Controlled pore glass is a glass that contains myriad, rather monodisperse pores winding throughout the interior of the particles. The particles are obtained by extracting a mixture of boron and silicon oxides, which was obtained from quenching from high temperature, with a basic aqueous solution. This solution dissolves the boron rich regions of the glass away leaving pores behind. One type of controlled pore glass that can be employed for this invention consists of ~100 micron $SiO_2$ particles that have pores approximately 300 nm diameter, a specific pore volume of ~1.25 $cm^3/g$ and a surface area of ~10 $m^2/g$.

The labeled CPG particles are prepared via decomposition of soluble solution phase precursors. Solutions of the nitrates, sulfates or other thermally decomposable anions of the ions required to form the host, absorber if needed, and rare earth emitter cations are dissolved into water. This solution which contains the atomically mixed elemental constituents, is imbibed into the pores of the CPG by placing the solution into contact with CPG particles that have been activated by heating to 200° C. under vacuum. The CPG whose pores are filled with the precursor solution are dehydrating by either (a) freeze drying the particles, (b) storing over a desiccant, (c) heating, (d) placing under reduced pressure or vacuum or (e) a combination of one of more of said methods (a), (b), (c) or (d) or other evaporative method. Freeze drying is a preferred method as the process inherently abrogates any potential phase segregation of the precursor constituents during dehydration. Next, the nitrate-filled CPG particles are heated in air, under vacuum or with another gas composition such as an argon/hydrogen mixture. After heating to a sufficiently high temperature, generally in the range of 300-900° C. depending on what the composition of the downconverting compositions material is, the nitrates or sulfates thermally decompose and give the downconverting composition material. For example, to prepare a CPG particle impregnated with the well known phosphor host $YVO_4$, doped with, for example, $Eu^{3+}$ cations to give $Y_{1-x}Eu_xVO_4$ where x is around 0.04, an aqueous solution containing the proper ratios of Y and Eu nitrates and vanadyl sulfate ($VOSO_4$) is prepared and an excess of this solution is placed onto the CPG powder. After removal of the excess aqueous solution, the liquid-filled particles are frozen at −20° C., placed under a vacuum and allowed to warm up at which point the sample undergoes freeze drying as the ice sublimes away leaving the dry, atomically mixed nitrate and sulfate precursors in the pores of the CPG. Next, the impregnated glass particles are heated to a sufficiently high temperature, for example about 850° C., the nitrates and sulfates are decomposed and thermolyzed to give $Y_{1-x}Eu_xVO_4$ which was identified from its visible emission spectrum. It is obvious to those skilled in the art that many other combinations of hosts, absorbers and emitters are possible in addition to the example listed here. Host examples include, without limitation, oxides such as yttrium oxide, yttrium vanadate, yttrium oxysulfide, aluminates including barium aluminate and yttrium aluminates such as YAG and $YAlO_3$, lanthanum oxide, zinc oxide, indium oxide, gadolinium oxysulfide as well as the vanadate, niobate, tungstate, phosphate and arsenates complexes of yttrium, lanthanum, lutetium and the alkaline earth metals. Various halides complexes, especially fluorides such as $NaYF_4$, or $YF_3$, are also suitable hosts. Emitters include +3 cations of Eu, Pr, Dy, Sm, Er, Ho, Tb, and Tm.

Example 8

Preparation of Downconverting Barcode Materials Based in Polymer Beads

Another useful form of the barcoded beads is based on dispersing the barcode particles into an organic polymer matrix. The phosphor particles are suspended in a solution containing the organic monomer from which the polymer will be made and conditions applied to cause the polymerization of the polymer with concomitant entrainment of the downconverting barcode particles. For example, small particles of $Y_{1-x}(RE)_xVO_4$ could be suspended in the solvent during the formation of polystyrene from styrene to give $Y_{1-x}(RE)_xVO_4$ impregnated polystyrene beads. The bead polymerization technology to entrain species other than downconverting materials (e.g. magnetic particles or organic dyes) is well known and is commercial well developed at companies like Bangs' Laboratories and Dynal Beads. Suitable points for the subsequent attachment of biomolecules, such as an amine functionality, could be derived from the incorporation of an appropriate amount of an alkylamino-substituted styrene into the styrene during the encoded particle preparation described above. Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for labeling a biological structure, the method comprising:
   providing a plurality of particles, each of the particles encoded with a downconverting composition which emits a detectable electromagnetic radiation upon excitation with an absorbable electromagnetic radiation, the emitted radiation defining a code;
   providing a plurality of probes;
   attaching one of the probes to one of the plurality of particles encoded with the downconverting composition; and
   combining the probe with a target biomolecule of the biological structure, the target biomolecule being complementary to the probe
   irradiating the biological structure with the absorbable electromagnetic radiation, the absorbable radiation having a first wavelength, the absorbable electromagnetic radiation inducing emissions from the downconverting composition at a radiation wavelength which is longer than the first wavelength, each of the emissions having a different wavelength range;
   measuring integrated intensities of the emissions; and
   calculating at least one relative ratio of the integrated emission intensities, the at least one relative ratio defining a code.

2. The method of claim 1, wherein the downconverting composition comprises a single lanthanide material having a host and two or more emitters, or two or more lanthanide materials each having a host and one or more emitters.

3. The method of claim 2, wherein the host is selected from a group consisting of oxides, oxysulfides, oxynitrides, aluminates, gallates, halides and combinations thereof.

4. The method of claim 2, wherein each of the emitters comprises a lanthanide material.

5. The method of claim 2, wherein each of the emitters is selected from a group consisting of gadolinium, europium, erbium, terbium, thulium, praseodymium, neodymium, dysprosium, samarium, holmium.

6. The method of claim 5, wherein at least some of the two or more emiters or the one or more emitters are different from one another.

7. The method of claim 1, wherein each of the particles further comprises a dye selected from the group consisting of rhodamines, cyanines, xanthenes, acridines, oxazines, porphyrins, phthalocyanines and combinations thereof.

8. The method of claim 1, wherein each of the particles further comprises a quantum dot selected from the group consisting of cadmium sulfide, lead selenide, lead telluride, zinc selenide, telluride and combinations thereof.

9. The method of claim 1, wherein the probe is selected from the group consisting of polynucleotides, DNA, RNA proteins, polypetides, antibodies and combinations thereof.

10. The method of claim 1, wherein the biological structure comprises a cell or sub-cellular structure.

11. A method for determining a location of a target biomolecule within a biological structure, the method comprising:
    combining a probe with the target biomolecule of the biological structure, the probe being attached to a particle encoded with a downconverting composition which emits a detectable electromagnetic radiation upon excitation with an absorbable electromagnetic radiation;
    irradiating the biological structure with the absorbable electromagnetic radiation, the absorbable radiation having a first wavelength, the absorbable electromagnetic radiation inducing emissions from the downconverting composition at a radiation wavelength which is longer than the first wavelength, each of the emissions having a different wavelength range;
    measuring integrated intensities of the emissions; and
    calculating at least one relative ratio of the integrated emission intensities, the at least one relative ratio defining a code;
    wherein the measuring of the integrated intensities and the calculation of the at least one relative ratio of the integrated emission intensities determine the location of the target biomolecule within the biological structure.

12. The method of claim 11, wherein the downconverting composition comprises a single lanthanide material having a host and two or more emitters, or two or more lanthanide materials each having a host and one or more emitters.

13. The method of claim 12, wherein the host is selected from a group consisting of oxides, oxysulfides, oxynitrides, aluminates, gallates, halides and combinations thereof.

14. The method of claim 12, wherein each of the emitters comprises a lanthanide material.

15. The method of claim 12, wherein each of the emitters is selected from a group consisting of gadolinium, europium, erbium, terbium, thulium, praseodymium, neodymium, dysprosium, samarium, and holmium.

16. The method of claim 15, wherein at least some of the two or more emiters or the one or more emitters are different from one another.

17. The method of claim 11, wherein each of the particles further comprises a dye selected from the group consisting of rhodamines, cyanines, xanthenes, acridines, oxazines, porphyrins, phthalocyanines and combinations thereof.

18. The method of claim 11, wherein each of the particles further comprises a quantum dot selected from the group consisting of cadmium sulfide, lead selenide, lead telluride, zinc selenide, telluride and combinations thereof.

19. The method of claim 11, wherein the probe is selected from the group consisting of polynucleotides, DNA, RNA proteins, polypetides, antibodies and combinations thereof.

20. The method of claim 11, wherein the biological structure comprises a cell or sub-cellular structure.

21. A method for determining an amount of target biomolecules within a biological structure, the method comprising:

combining probes with the target biomolecules of the biological structure, each of the probes being attached to a particle encoded with a downconverting composition which emits a detectable electromagnetic radiation upon excitation with an absorbable electromagnetic radiation;

irradiating the biological structure with the absorbable electromagnetic radiation, the absorbable radiation having a first wavelength, the absorbable electromagnetic radiation inducing emissions from the downconverting composition at a radiation wavelength which is longer than the first wavelength, each of the emissions having a different wavelength range;

measuring integrated absolute intensities of the emissions;

calculating relative ratios of the integrated emission intensities, each of the relative ratios defining a code; and using the absolute intensities of the emissions and the relative ratios to determine the amount of the target biomolecules within the biological structure.

22. The method of claim 21, wherein the downconverting composition comprises a single lanthanide material having a host and two or more emitters, or two or more lanthanide materials each having a host and one or more emitters.

23. The method of claim 22, wherein the host is selected from a group consisting of oxides, oxysulfides, oxynitrides, aluminates, gallates, halides and combinations thereof.

24. The method of claim 22, wherein each of the emitters comprises a lanthanide material.

25. The method of claim 22, wherein each of the emitters is selected from a group consisting of gadolinium, europium, erbium, terbium, thulium, praseodymium, neodymium, dysprosium, samarium, and holmium.

26. The method of claim 25, wherein at least some of the two or more emiters or the one or more emitters are different from one another.

27. The method of claim 21, wherein each of the particles further comprises a dye selected from the group consisting of rhodamines, cyanines, xanthenes, acridines, oxazines, porphyrins, phthalocyanines and combinations thereof.

28. The method of claim 21, wherein each of the particles further comprises a quantum dot selected from the group consisting of cadmium sulfide, lead selenide, lead telluride, zinc selenide, telluride and combinations thereof.

29. The method of claim 21, wherein the probe is selected from the group consisting of polynucleotides, DNA, RNA, proteins, polypetides, antibodies and combinations thereof.

30. The method of claim 21, wherein the biological structure comprises a cell or sub-cellular structure.

* * * * *